United States Patent [19]

Johnson

[11] Patent Number: 5,118,297
[45] Date of Patent: Jun. 2, 1992

[54] OBTURATOR BODY FOR USE IN FILLING AN ENDONTICALLY PREPARED ROOT

[76] Inventor: William B. Johnson, 5010 E. 68th St., Ste. 104, Tulsa, Okla. 74136

[21] Appl. No.: 640,047

[22] Filed: Jan. 9, 1991

[51] Int. Cl.$^5$ ............................................... A61C 5/02
[52] U.S. Cl. ...................................... 433/224; 433/81
[58] Field of Search ........................... 433/81, 102, 224

[56] References Cited

U.S. PATENT DOCUMENTS

| | | | |
|---|---|---|---|
| 3,919,774 | 11/1975 | Fishman | 433/224 |
| 4,321,040 | 3/1982 | Miller et al. | 433/102 |
| 4,457,710 | 7/1984 | McSpadden | 433/81 |
| 4,758,156 | 7/1988 | Johnson | 433/81 |

FOREIGN PATENT DOCUMENTS

| | | | |
|---|---|---|---|
| 1220369 | 4/1987 | Canada | 433/81 |
| 2724516 | 4/1978 | Fed. Rep. of Germany | 433/81 |

*Primary Examiner*—John J. Wilson
*Attorney, Agent, or Firm*—Head and Johnson

[57] ABSTRACT

An improved obturator body for use in filling an endodontically prepared root canal formed of an elongated slender body of plastic material having a proximal end and a distal end, the body having a short length handle portion at the proximal end and a shaft portion extending from the handle portion to the distal end, the shaft portion being dimensioned to be received in an endodontically prepared root and having a texture surface adapted to receive filler material thereon and a plurality of integral spaced apart length indicators formed on the exterior surface of the shaft portion for indicating the length of the shaft to the distal end. In one preferred arrangement, the body shaft portion has canal filler material, such as gutta-percha, formed thereon.

14 Claims, 1 Drawing Sheet

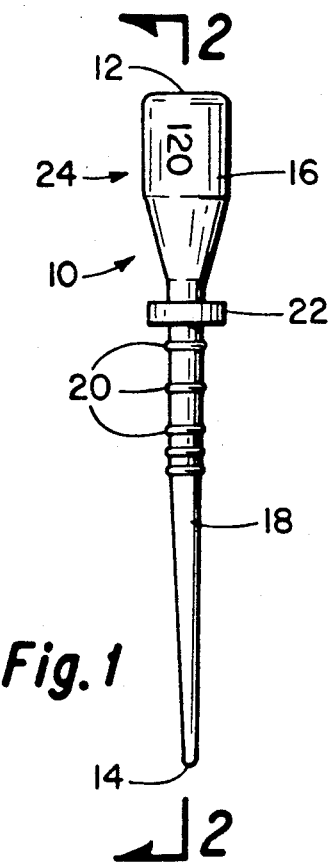
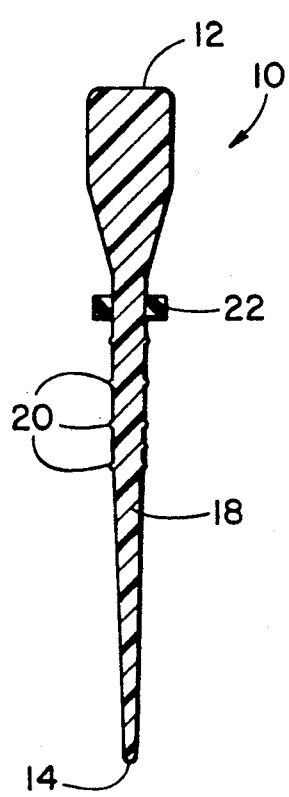
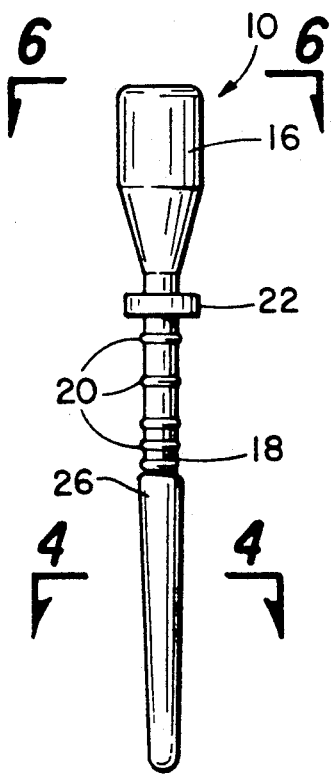
Fig. 1
Fig. 2
Fig. 3
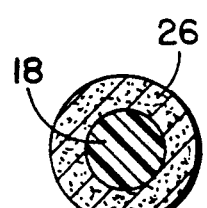
Fig. 4
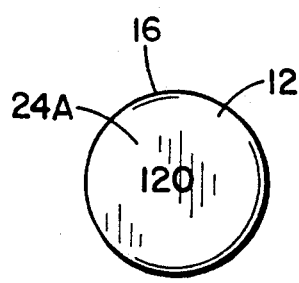
Fig. 6
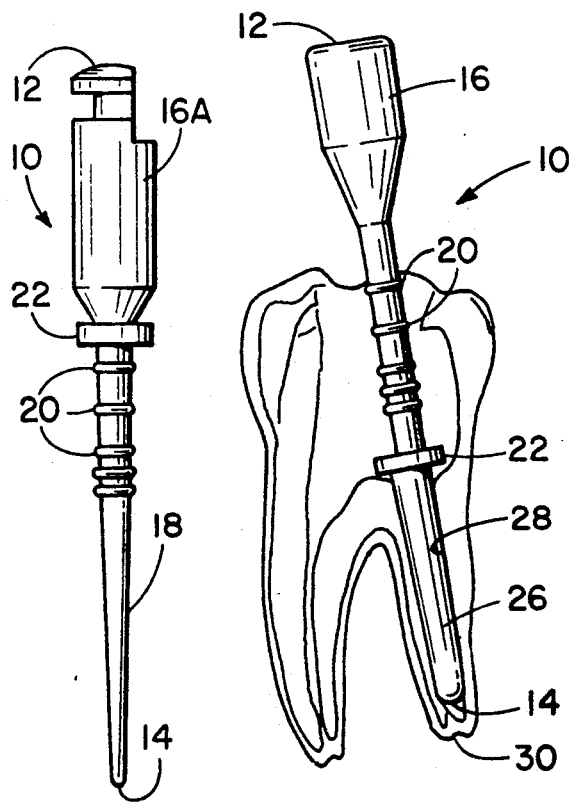
Fig. 7
Fig. 5

OBTURATOR BODY FOR USE IN FILLING AN ENDONTICALLY PREPARED ROOT

BACKGROUND OF THE INVENTION

This disclosure is related to the subject matter of U.S. Pat. No. 4,758,156 issued Jul. 19, 1988, to William B. Johnson, entitled "A Tool For Use In Applying Filler Material To An Endodontically Prepared Root Canal" and U.S. Pat. No. 4,894,011 issued Jan. 16, 1990, to William B. Johnson, entitled "Appliance For Use In Applying Filler Material To An Endodontically Prepared Root Canal," both of which patents are incorporated herein by reference.

As pointed out in the two above-identified U.S. patents, the conventional technique for preforming endodontic therapy on teeth is time consuming and often does not adequately ensure that the entire canal system is filled with the filler material. Experience has shown that it is not possible in all cases to remove all pulpal remnants and contaminants from a root canal with currently used preparation techniques. If the pulpal remnants and contaminations are thoroughly entombed in the repair material, the endodontic therapy will be successful. If the remnants and contaminants are not thoroughly entombed, there is high probability of failure of the endodontic therapy. Complete entombment of the remnants and contaminants requires complete obturation of the canal system.

The general technique employed by dentists in the United States and throughout the world prior to the above two mentioned U.S. patents consisted of packing a filler material, such gutta-percha, into the endodontically prepared root canal.

The technology employed in the above two mentioned U.S. patents has improved the practice of filling endodontically prepared root canals by making use of an obturator body having filler material thereon. After the root canal is prepared, the obturator body is inserted into the root canal, carrying with it, on the exterior surface thereof, filler material. The shaft portion of the obturator body and filler material remain in the prepared canal to more effectively fill the canal and entomb any remaining pulpal material or contaminants, and such system has been commercially successful and widely practiced by dentists and endodontists.

The obturator body shaft portion functions as a condenser of the filler material and assists in plugging the root canal. Further, the obturator body shaft portion remaining in the root canal helps reduce the effect of shrinkage of the filler material.

The present disclosure is of an improved obturator body that is particularly characterized by improved means of enabling a dental practitioner to accurately position the body shaft portion to the proper depth in a root canal by the provision of effective length indicators.

SUMMARY OF THE INVENTION

The present disclosure is an improved obturator body for use in filling an endodontically prepared root canal. The obturator body is in the form of an elongated slender body of plastic material. The obturator body has a proximal end and a distal end with a handle portion at the proximal end. The body further includes an integral shaft portion extending from the handle portion to the distal end. Such shaft portion has a surface adapted to receive filler material thereon.

Integrally formed on the shaft portion in the area adjacent the handle portion are a plurality of spaced apart length indicators. These length indicators are used to indicate the length of the shaft portion to the distal end.

In one embodiment of the invention, canal filler material, such as gutta-percha, is formed on the body shaft portion so that an obturator is provided as an appliance ready for use by a dental practitioner to fill an endodontically prepared root canal.

In the process of an endodontic treatment the endodontist or other dental practitioner, after carefully cleaning and preparing a root canal and removing, as thoroughly as possible, the pulpal material and contaminants from the canal, then employs the obturator body of this disclosure for filling the canal. One highly varying aspect of root canals is the depth or length thereof. The endodontist or dental practitioner in preparing a root canal typically utilizes elongated cylindrical files. In the usual practice, the practitioner determines that the therapy has been completed to remove the pulpal material to the full length of the root canal by an X-ray picture with the file in position in the canal. The endodontist can then determine from such X-ray picture that the file has prepared the root canal to the terminal end thereof. The endodontist can then determine from such file the length of an obturator necessary to fully fill the prepared root canal.

By the employment of the principals of the present disclosure, the proper length is readily indicated upon the obturator body shaft portion. The obturator body may, in one embodiment, include filler material thereon, and, therefore, the practitioner can insert the obturator with the filler material thereon in the prepared canal to the proper depth as indicated by markers on the obturator body shaft portion, assuring complete filling of the root canal.

The obturator body of the present disclosure is formed of plastic material. Plastic has advantages compared to most metals as an obturator body, including biological inertness, flexibility, ease of manufacture and reduced expense. Further, a root canal filled using a plastic obturator is easier to re-treat or to create post space, if necessary, than a tooth filled with a metal obturator body since a plastic obturator body can be easily drilled if necessary.

Obturator bodies of the present disclosure are preferably provided by a manufacturer to practitioners in sets of varying diameters. The practitioner can then select the obturator body shaft diameter appropriate for the canal being filled. Each obturator body in a set preferably has the nominal diameter indicated on the handle portion.

A better understanding of the invention will be had by reference to the following description and claims, taken in conjunction with the attached drawings.

DESCRIPTION OF THE DRAWINGS

FIG. 1 is an elevational view of an obturator body for use in filling an endodontically prepared root canal having an integral manually manipulative handle portion.

FIG. 2 is a cross-sectional view taken along the line 2—2 of FIG. 1.

FIG. 3 is an external view of the obturator body of FIG. 1 showing filler material formed on the body shaft portion illustrating one method of use of the obturator body for filling a prepared root canal.

FIG. 4 is a cross-sectional view taken along the line 4—4 of FIG. 3 showing the filler material formed about the obturator body shaft portion.

FIG. 5 is a cross-sectional view of a tooth having an endodontically prepared root canal and showing the appliance of FIG. 3 inserted within the prepared root canal.

FIG. 6 is an end view of an obturator body manually manipulative handle portion showing a size indicator thereon.

FIG. 7 is an elevational view of an obturator body for use in filling an endodontically prepared root canal as in FIG. 1 but showing the arrangement wherein the handle portion is configured to be received in a dental tool.

DESCRIPTION OF THE PREFERRED EMBODIMENT

Referring to FIGS. 1 and 2, the improved obturator body for use in providing an endodontic filler appliance is illustrated and indicated generally by the numeral 10. The obturator body is an elongated slender apparatus of plastic material having a proximal end 12 and a distal end 14. At the proximal end 12 is an enlarged diameter handle portion 16 that is of relatively short length and integral with the other portions of the obturator body.

Extending from the handle portion 16 to the distal end 14 is a shaft portion 18. The shaft portion 18 is preferably slightly tapered and has a textured or mat finished external surface that is adaptable to receive and retain filler material thereon.

Integrally formed on shaft portion 18 are a plurality of spaced apart length indicators 20. The length indicators are preferably in the form of short length increased external diameter integrally formed circumferential ridges. Length indicators 20 are preferably spaced at selected distances measured in millimeters from distal end 14.

Received on the obturator shaft portion 18, adjacent the handle portion 16, is a sliding stopper or washer 22, preferably made of rubber or of plastic material having similar characteristics to rubber.

In the employment of the apparatus of this disclosure the preferred practice is that obturator 10 be provided in sets having shaft portions 18 of varying nominal diameters. The diameter of prepared root canals varies considerably and for effectively filling an endodontically prepared root canal, an obturator having a shaft portion 18 of a diameter which is less than but approximates that of the root canal is preferred. For this reason, the obturators are typically supplied in sets of varying shaft diameters. The shaft diameter is preferably visually indicated on the handle, as indicated by the numeral 24. Alternatively, the nominal diameter may be indicated on the handle proximal end 12 as indicated by 24A in FIG. 6.

FIG. 2 is a cross-sectional view of an obturator body 10 with the length indicators 20 integrally formed thereon as circumferential increased external diameter portions, and with stopper 22.

FIG. 3 shows an appliance in the form as used for filling a root canal. The appliance includes the obturator body 10 of FIGS. 1 and 2 wherein the shaft portion 18 has filler material 26 formed thereon. Typically, filler material 26 is applied to shaft portion 18 by subjecting filler material and the obturator body to an elevated temperature for a selected length of time to cure filler material 26 so that it securely adheres to shaft portion 18 but remains pliable for insertion into an endodontically prepared root canal.

FIG. 4 shows a cross-section of shaft 18 with filler material 26 thereon.

FIG. 5 is a cross-sectional view of a representative tooth configuration having an endodontically prepared root canal 28 therein and showing the obturator of this disclosure being employed to fill the root canal. The obturator shaft portion 18 having filler material 26 thereon has been positioned within canal 28. By use of the length indicators 20, the endodontist knows that the obturator has been inserted so that the filler material is carried to the apex 30 of the canal. Stopper 22 is used to retain the filler material in the canal, as the handle portion 16 and the unused portion of the shaft 18 is removed. By use of the length indicators 20, the endodontist verifies that the shaft portion having the filler material 26 thereon has been inserted to the proper depth within the root canal, and the endodontist can then sever the shaft portion at the proper location and remove the handle portion 16, the unused shaft portion 18 and washer 22, leaving the required length of the shaft portion 18 and filler material 26 within the root canal.

In the preferred arrangement the material of which the obturator body 10 is formed, and particularly the shaft portion 18, is of X-ray opaque. In this manner, after the appliance has been inserted into a tooth the endodontist can verify, by X-ray, that the obturator body shaft 18 having the filler material thereon has been carried to adjacent the root apex 30 so that the canal is completely filled to the full depth. As an example of one method of providing an X-ray opaque plastic, powered tungsten may be mixed with plastic at a ratio of about 50/50 by weight.

The obturator body 10 is, as has been previously stated, preferably formed of plastic material. The plastic material employed must be biologically inert and nonbiodegradable in the environment in which it is used, and must have strength in combination with flexibility. A plastic material that has been successfully employed in manufacturing prototypes is UDEL polysulfone MG-11, sold by AMOCO Performance Products, Inc. of Ridgefields, Conn. "UDEL" is a registered trademark of Union Carbide Corporation.

Another plastic material that has shown promise in the construction of test obturator is liquid crystal polymer, such as Vectra VC-3 manufactured by Hoechst Celanese Corporation of Chatham, N.J.

FIG. 7 is shown as an alternate embodiment of the obturator body of this disclosure having a handle portion 16A configured to be received in a dental tool. Typically handle portion 16A is configured to correspond to dental drills or dental burrs that are insertable in a dental handpiece. While the handle configuration of FIG. 7 can be used to manually install an appliance in an endodontically prepared root canal, the preferred obturator body for manual use is illustrated in FIGS. 1, 2, 3, and 5, while the embodiment of FIG. 7 is designed for use in a handpiece.

The claims and the specification described the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. An obturator body for use in filling an endodontically prepared root canal, comprising:
    an elongated slender body having a proximal end and a distal end, the body having a handle portion at said proximal end, the body having a shaft portion from the handle portion to said distal end, such shaft portion being dimensioned so that the portion thereof adjacent said distal end may be received in an endodontically prepared root canal and such portion has a surface adapted to receive filler material thereon;
    a plurality of integral spaced apart length indicators formed on the exterior surface of said body shaft portion between said handle portion and said portion adjacent said distal end to be received in an endodontically prepared root canal, the indicators serving to indicate the length of said shaft portion to said distal end; and
    canal filler material formed on said body shaft portion adjacent said distal end leaving at least a substantial portion of said length indicators visually exposed.

2. An obturator body for use in filling an endodontically prepared root canal according to claim 1 wherein said length indicators are in the form of integral short length increased external diameter portions.

3. An obturator body for use in filling an endodontically prepared root canal according to claim 1 including an elastomeric washer member having an opening therethrough slideably received on said body shaft portion adjacent said handle portion.

4. An obturator body for use in filling an endodontically prepared root canal according to claim 1 wherein said filler material formed on said body shaft portion extends beyond said distal end thereof.

5. An obturator body for use in filling an endodontically prepared root canal according to claim 1 wherein said body shaft portion is of cylindrical cross-sectional configuration.

6. An obturator body for use in filling an endodontically prepared root canal according to claim 1 wherein said canal filling material is gutta-percha.

7. An obturator body for use in filling an endodontically prepared root canal according to claim 1 wherein said body is made of a plastic material selected from the group comprising polysulfone, and liquid crystal polymer.

8. An obturator body for use in filling an endodontically prepared root canal according to claim 1 wherein said body shaft portion has a textured surface for improving the adherence of filler material thereon.

9. An obturator body for use in filling an endodontically prepared root canal according to claim 1 wherein said body shaft portion is slightly tapered from adjacent said handle portion to said distal end.

10. An obturator body for use in filling an endodontically prepared root canal according to claim 1 wherein at least said body shaft portion is X-ray opaque.

11. An obturator body for use in filling an endodontically prepared root canal according to claim 1 wherein said handle portion is configured to be received in and removably retained by a dental tool.

12. An obturator body for use in filling an endodontically prepared root canal according to claim 1 including visual size indicia imprinted on said handle portion indicating the nominal diameter of said shaft portion.

13. An obturator body for use in filling an endodontically prepared root canal according to claim 1 wherein said handle portion is configured for manual manipulation of said body.

14. An obturator for use in filling an endodontically prepared root canal according to claim 1 wherein said canal filler material is cured on said body shaft portion adjacent said distal end by application of elevated temperature for a selected length of time.

* * * * *

UNITED STATES PATENT AND TRADEMARK OFFICE
CERTIFICATE OF CORRECTION

PATENT NO. : 5,118,297
DATED : June 2, 1992
INVENTOR(S) : William B. Johnson

It is certified that error appears in the above-indentified patent and that said Letters Patent is hereby corrected as shown below:

On the title page, Item [54]  change "ENDONTICALLY" to --ENDODONTICALLY --
insert -- CANAL-- after "ROOT"

Column 1, line 3,  change "ENDONTICALLY" to --ENDODONTICALLY --
insert -- CANAL -- after "ROOT"

Signed and Sealed this

Third Day of August, 1993

Attest:

MICHAEL K. KIRK

Attesting Officer          Acting Commissioner of Patents and Trademarks